United States Patent [19]

Veith et al.

[11] Patent Number: 5,516,569

[45] Date of Patent: May 14, 1996

[54] HIGH ABSORBENCY COMPOSITE

[75] Inventors: Michael W. Veith, Oshkosh, Wis.; Francis P. Abuto, Alpharetta, Ga.; Edward E. Werner, Oshkosh; Anthony J. Wisneski, Kimberly, both of Wis.

[73] Assignee: Kimberly-Clark Corporation, Neenah, Wis.

[21] Appl. No.: 132,424

[22] Filed: Oct. 5, 1993

Related U.S. Application Data

[63] Continuation of Ser. No. 805,126, Dec. 11, 1991, abandoned.

[51] Int. Cl.$^6$ ............................. A61F 13/15; B32B 5/16
[52] U.S. Cl. ............................. 428/68; 428/76; 428/156; 428/170; 428/171; 428/195; 428/220; 428/283; 428/323; 604/367; 604/368; 604/374; 604/385.1
[58] Field of Search .................. 428/68, 76, 283, 428/156, 170, 171, 195, 220, 323; 604/367, 368, 374, 385.1

[56] References Cited

U.S. PATENT DOCUMENTS

| | | | |
|---|---|---|---|
| 4,103,062 | 7/1978 | Aberson et al. | 428/283 |
| 4,186,165 | 1/1980 | Aberson et al. | 264/112 |
| 4,252,761 | 2/1981 | Schoggen et al. | 264/120 |
| 4,460,642 | 7/1984 | Errede | 604/367 |
| 4,551,142 | 11/1985 | Kopolow | 604/368 |
| 4,560,372 | 12/1985 | Pieniak | 604/369 |
| 4,610,678 | 9/1986 | Weisman et al. | 604/368 |
| 4,645,698 | 2/1987 | Matsubara | 604/368 |
| 4,675,209 | 6/1987 | Pedigrew | 427/194 |
| 4,826,880 | 5/1989 | Lesniak et al. | 521/53 |
| 4,879,170 | 11/1989 | Radwanski et al. | 428/233 |
| 4,886,697 | 12/1989 | Perdelwitz | 604/367 |
| 5,156,902 | 10/1992 | Pieper | 428/206 |

FOREIGN PATENT DOCUMENTS

| | | |
|---|---|---|
| 0085729 | 8/1983 | European Pat. Off. . |
| 0138427 | 4/1985 | European Pat. Off. . |
| 0146190 | 6/1985 | European Pat. Off. . |
| 0157649 | 10/1985 | European Pat. Off. . |
| 0172035 | 2/1986 | European Pat. Off. . |
| 0198683 | 10/1986 | European Pat. Off. . |
| 0202125 | 11/1986 | European Pat. Off. . |
| 0217766 | 4/1987 | European Pat. Off. . |
| 0254476 | 1/1988 | European Pat. Off. . |
| 0255654 | 2/1988 | European Pat. Off. . |
| 0301772 | 2/1989 | European Pat. Off. . |
| 0304319 | 2/1989 | European Pat. Off. . |
| 0309187 | 3/1989 | European Pat. Off. . |
| 0325416 | 7/1989 | European Pat. Off. . |
| 0339461 | 11/1989 | European Pat. Off. . |
| 0374910 | 6/1990 | European Pat. Off. . |
| 0426197 | 5/1991 | European Pat. Off. . |
| 0426227 | 5/1991 | European Pat. Off. . |
| 0443627 | 8/1991 | European Pat. Off. . |

*Primary Examiner*—Nasser Ahmad
*Attorney, Agent, or Firm*—Jeffrey B. Curtin

[57] ABSTRACT

Disclosed is an absorbent composite including a web formed from a mixture of fibrous material and particulate absorbent material. The web contains from about 15 to about 30 weight percent water. The described absorbent web is capable of containing relatively large quantities of particulate absorbent materials while maintaining an acceptable degree of flexibility.

20 Claims, 4 Drawing Sheets

HIGH ABSORBENCY COMPOSITE

This is a continuation of application Ser. No. 07/805,126 filed on Dec. 11, 1991 now abandoned.

BACKGROUND OF THE INVENTION

1. Field of the Invention

The present invention relates to absorbent composites comprising a fibrous material and a relatively large quantity of a particulate, water-swellable, generally water-insoluble absorbent material.

2. Description of the Related Art

Absorbent composites suitable for use in absorbent products such as diapers, training pants, feminine care products, adult incontinence products, and the like are known. As a general rule, the absorbent composites comprise a matrix of fibers. The fiber matrixes tend to have a relatively low specific absorption capacity. Accordingly, absorbent products requiring a relatively high absorbent capacity, and employing such a fiber matrix, tend to be relatively thick and bulky. In an attempt to increase the absorbent capacity of such fiber matrixes, absorbent materials, known in the art as superabsorbents, have been introduced into the fiber matrixes. As a general rule, the fiber of the matrix and the absorbent material are combined in an airstream and deposited on a porous forming surface. Such structures are generally lofty and soft.

In an attempt to produce thinner absorbent composites and products, higher concentrations of absorbent material have been added to the fibers in an attempt to maintain absorption capacity of the absorbent composites while reducing their overall bulk. Unfortunately, the amount of absorbent material that can be contained within a fibrous matrix, due to fiber entrapment, is limited. When this limit is exceeded, the absorbent material present in the fiber matrix tends to migrate out of the fiber matrix during manufacture and transport of the absorbent product. When this occurs, the absorbent material may contact the skin of a user. This is undesirable.

Various methods have been suggested to overcome the problem of containing absorbent material within a fibrous matrix. For example, European Patent 0 085 729 published Nov. 6, 1985, describes a process wherein a fusion adhesive is used to adhere particles of an absorbent material to a substrate. European Patent Application 0 301 772 published Feb. 1, 1989, describes a particle-bonded, nonwoven fibrous web containing liquid-absorbent polymer particles distributed therein and attached to the fibers by the use of an adhesive binder. European Patent Application 0 255 654 describes a process employing a resin binder to adhere absorbent polymer particles in a cellulose fiber web. Lesniak et al. U.S. Pat. No. 4,826,880 issued May 2, 1989, describes absorbent products containing hydrates of particulate absorbent polymers.

The use of adhesive binders, thermoplastic resins, and the like may be sufficient to adhere particles of absorbent material in a fibrous web but may undesirably affect the flexibility of the web and may prove to be too costly or complicated for use in disposable absorbent products.

SUMMARY OF THE INVENTION

Accordingly, it is desirable to produce an absorbent composite formed from fibers and a relatively large amount of particulate absorbent material, which absorbent composite is capable of containing the particulate absorbent material and maintaining an acceptable level of softness and flexibility to render it suitable for use in disposable absorbent products.

The present invention concerns an absorbent composite comprising a compressed absorbent web. The web comprises a mixture of from about 0 to about 45 weight percent, based on total mixture weight, of a fibrous material; from about 40 to about 85 weight percent, based on total mixture weight, of a particulate, water-swellable, generally water-insoluble absorbent material capable of absorbing at least about 10 times its own weight in water; and from about 15 to about 30 weight percent, based on total mixture weight, of water. As formed, bonding occurs between the fibrous material and absorbent material such that the absorbent material is substantially contained within said absorbent web. In a preferred embodiment, a liquid-permeable wrap sheet at least partially surrounds the web.

In a second aspect, the present invention concerns a method of forming an absorbent composite, the method involves forming an absorbent web, said web comprising a mixture of from about 0 to about 45 weight percent, based on total mixture weight, of a fibrous material; from about 40 to about 85 weight percent, based on total mixture weight, of a particulate, water-swellable, generally water-insoluble absorbent material capable of absorbing at least about 10 times its own weight in water; and from about 15 to about 30 weight percent, based on total mixture weight, of water. At least a portion of a surface of said absorbent web is then surrounded with a liquid-permeable wrap sheet. The absorbent web is then compressed such that bonding occurs between the fibrous material and absorbent material, whereby the absorbent material is substantially contained within the absorbent web.

DETAILED DESCRIPTION OF THE PREFERRED EMBODIMENT

Figure 1:
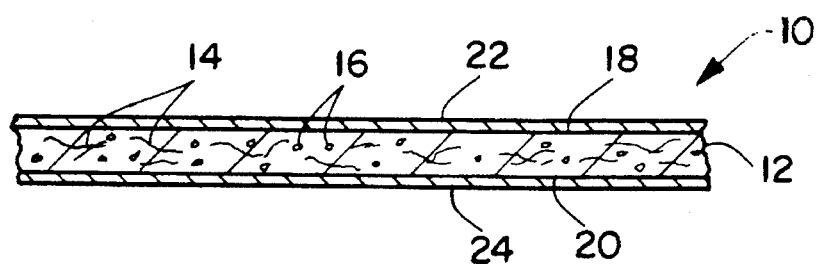
FIG. 1 illustrates an absorbent composite according to a first embodiment of the present invention.

The present invention relates to an absorbent composite. The absorbent composite comprises a compressed absorbent web. The absorbent web comprises a mixture of a fibrous material, a particulate, water-swellable, generally water-insoluble absorbent material, and water.

Fibers suitable for use in the present invention include cellulosic fibers such as wood pulp, cotton linters, cotton fibers, and the like; synthetic polymeric fibers such as polyolefin fibers, polyamide fibers, polyester fibers, polyvinyl alcohol fibers, polyvinyl acetate fibers, synthetic polyolefin wood pulp fibers, and the like; as well as regenerated cellulose fibers such as rayon and cellulose acetate fibers and microfibers. Mixtures of various fiber types are also suitable for use in the present invention. For example, a mixture of cellulosic fibers and synthetic polymeric fibers may be used.

As a general rule, the fibers will have a length-to-diameter ratio of at least about 5:1, preferably at least 10:1. As used herein, "diameter" refers to a true diameter if generally circular fibers are used or to a maximum transverse cross-sectional dimension if non-circular, e.g., ribbon-like, fibers are used. The fibers will generally have a length of from about 0.5 millimeter to about 25 millimeters, preferably of from about 1 millimeter to about 10 millimeters. Fiber diameters will generally be from about 0.001 millimeter to about 1 millimeter, preferably from about 0.005 millimeter to about 0.01 millimeter. For reasons such as economy, availability, physical properties, and ease of handling, cellulosic wood pulp fibers are preferred for use in the present invention.

As used herein, the term "absorbent material" refers to a water-swellable, generally water-insoluble material capable of absorbing at least about 10, desirably about 20, and preferably about 100 times or more its weight in water. The absorbent material may be formed from organic material, which may include natural materials such as agar, pectin, and guar gum, as well as synthetic materials such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropylcellulose, polyvinylmorpholinone, polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the materials substantially water insoluble. Crosslinking may, for example, be by irradiation or covalent, ionic, Van der Waals, or hydrogen bonding. Suitable materials are available from various commercial vendors such as the Dow Chemical Company, Hoechst Celanese Corporation, Allied Colloid Inc., and Stockhausen Inc. The non-cellulosic, synthetic hydrogel polymers are preferred for use in the present invention. In one preferred embodiment, the absorbent material is selected from the group consisting of alkali metal salts of polyacrylic acid, polyacrylamides, polyvinyl alcohol, ethylene maleic anhydride copolymers, polyvinyl ethers, polyvinylmorpholinone, polymers and copolymers of vinyl sulfonic acid, polyacrylates, polyacrylamides, polyvinylpyrridines, hydrolyzed acrylonitrile grafted starch, acrylic acid grafted starch, and isobutylene maleic anhydride copolymers and mixtures thereof.

The absorbent material is in the form of discrete particles. As a general rule, the discrete particles will have a maximum cross-sectional dimension of from about 10 micrometers to about 2,000 micrometers, preferably of from about 60 micrometers to about 1,000 micrometers. In one preferred embodiment, the discrete particles have an irregular, non-spherical, non-fibrous shape. The irregularly shaped particles are believed to present surfaces which are more easily contained in the absorbent webs of the present invention. Such irregularly shaped discrete particles are suitably formed by grinding or otherwise comminuting relatively large blocks of absorbent material into irregularly shaped particles having the described maximum cross-sectional dimension. For example, when the absorbent material is an alkali metal salt of poly(acrylic acid), the absorbent material is suitably formed through a gel or solution polymerization process, dried, and the resultant material ground into irregularly shaped discrete particles having the desired size.

The fibrous material, absorbent material, and water are combined to form a mixture comprising from about 0 to about 45, beneficially from about 0 to about 35, desirably from about 5 to about 30, and preferably from about 10 to about 25 weight percent, based on total mixture weight, of the fibrous material; from about 40 to about 85, beneficially from about 50 to about 85, desirably from about 55 to about 80, preferably from about 60 to about 80 weight percent, based on total weight of the mixture, of the particulate absorbent material; and from about 15 to about 30, beneficially from about 15 to about 25 and preferably from about 15 to about 22 weight percent, based on total mixture weight, of water.

As used herein, reference to the amount of water contained in the mixture refers to the weight of water present in the mixture divided by the total weight of the mixture including the water present therein. Thus, the amount of water present in the mixture can be determined by weighing the mixture, including the weight of the water present therein (starting weight), subsequently exposing the mixture to conditions sufficient to evaporate essentially all of the water present therein and weighing the mixture (dry weight). The amount of water originally present in the mixture, based on weight percent, can then be calculated according to the following formula:

$$\frac{\text{(starting weight)} - \text{(dry weight)}}{\text{(starting weight)}} \times 100$$

Conditions suitable for evaporating essentially all of the water present in the web are known to those skilled in the art. For example, the web can be exposed to a temperature of about 105° C. for a period of about 24 hours.

Those skilled in the art will recognize that some of the fibrous materials described as suitable for use in the present invention will generally contain a certain amount of water at ambient conditions. For example, cellulosic wood pulp may generally have from about 2 to about 8 weight percent water contained therein as supplied at ambient conditions. Similarly, absorbent materials suitable for use in the present invention may contain a certain amount of water in the form in which the materials are supplied. For example, alkali metal salts of poly(acrylic acid) are generally supplied for use in disposable diapers in a form which contains about 4 to 8 weight percent water. The total amount of water present in the mixture includes that originally present in the fibrous material and absorbent material.

Applicants have found that, by having about 15 to 30 weight percent of water present in the mixture, good containment of the absorbent material may be achieved even at relatively high concentrations of absorbent material. This containment can be achieved while maintaining an acceptable level of flexibility and softness in the webs.

At moisture contents less than about 15 weight percent, flexible webs can be formed. Unfortunately, the webs are generally not as well suited to contain relatively large amounts (greater than about 40 weight percent) of particulate absorbent material. At even higher concentrations of absorbent material, for example, 50, 60 or 80 weight percent, containment of the absorbent material becomes even more difficult. At moisture contents of greater than about 30 weight percent, good containment may be achieved. Unfortunately, the webs tend to have a wet feel and may be conducive to bacterial growth. The wet feel may be corrected by drying. Drying may, however, produce undesirable stiffening of the product.

Water can be mixed with the fibrous material and absorbent material in any suitable way. For example, the water may be added to the fibrous and absorbent materials prior to mixing, during mixing, or may be applied to the web after mixing. Those skilled in the art will recognize suitable means for applying water to the webs. The water may be applied as a liquid or in gaseous form. In one preferred embodiment, the water is applied to the web after formation of the mixture of fibrous material and absorbent material and is applied in the form of a liquid.

The web may be at least partially surrounded by a liquid-permeable wrap sheet. Those skilled in the art will recognize materials suitable for use as wrap sheets. Exemplary of suitable materials are nonwoven webs formed from cellulosic fibers, e.g., wet-formed tissues, or nonwoven webs formed from synthetic polymeric materials. As a general rule, the wrap sheet has a basis weight of from about 5 grams per square meter to about 50 grams per square meter, preferably of from about 15 grams per square meter to about 25 grams per square meter.

The wrap sheet is generally of a porosity which will allow a significant number of the particles of absorbent material to pass therethrough. Accordingly, the wrap sheet does not generally significantly assist in containment of the absorbent material by presenting an impenetrable barrier. The wrap sheet may assist in containment of the absorbent material by providing a surface to which the absorbent materials can adhere. If it is desired, the wrap sheet may have a porosity which prevents passage of a majority of the absorbent material. In this way, better containment of the absorbent material may be achieved.

In the preferred embodiment, the wrap sheet comprises a tissue formed from cellulosic fibers. The wrap sheet may surround only a portion of the web or may completely surround the web. To assist in containment of the particulate absorbent material, it is often preferred that the wrap sheet completely surround the web. The wrap sheet may be C-folded or D-folded around the web.

It is hypothesized that the improved containment of absorbent material of the absorbent web, according to the present invention, results from bonding occurring between the particles of absorbent material and the fibers, as well as between the particles of absorbent material and other particles of absorbent material, and between the fibers themselves. When a wrap sheet is present, additional bonding may occur between the components of the web and the wrap sheet. It is the various types of bonding which Applicants believe accounts for the good containment of the absorbent material. It is often desired that substantial bonding occur in the absorbent webs. While the bonding does inevitably lead to a somewhat stiffer web, Applicants have found that, by carefully controlling the relative concentrations of fibrous material, absorbent material, and water, good containment can be achieved while maintaining an acceptable level of flexibility.

Once the bonding has occurred, it may be possible to dry the web to a degree without destroying the bonding or introducing an unacceptable level of stiffness. For example, if the web is manufactured to contain 20 weight percent water, it may be possible to dry several weight percent of water from the web without lowering the containment achieved with 20 weight percent water. Similarly, if the web is manufactured to contain 15 weight percent water, it may be possible to dry several weight percent of water from the web and still maintain the containment achieved prior to the drying. Nonetheless, to achieve the desired containment, the web should, at some point, contain at least 15 weight percent water.

Webs of cellulosic fiber and absorbent material, not comprising at least about 15 weight percent water, tend to laterally separate, pull apart or rope after wetting. When this happens, subsequent insults of liquid pass through the web and tend to leak. The absorbent webs, according to the present invention, possess good wet integrity. Specifically, the webs resist lateral separation after wetting. Accordingly, the webs of the present invention tend to resist leakage better than many known webs. This improved wet integrity is particularly evident in webs comprising relatively high concentrations of absorbent material. Specifically, webs comprising at least 50, and preferably 60, weight percent of absorbent material possess improved wet integrity. This is due, in part, to the gel-like nature of the web when wet.

In order to further assist with containment of the absorbent material, it is sometimes desirable to calender or emboss the webs of fibrous material, absorbent material and water. While calendering of the entire web is possible, Applicants have found that, to reduce stiffness of the webs and damage (crushing) of the absorbent material particles, it is often desirable to employ patterned embossing rolls as opposed to calendering the entire web. The embossing rolls suitably form an embossed pattern over a relatively low amount of the surface area of the web. For example, suitably less than about 10 percent, beneficially less than about 8 percent, and preferably less than about 5 percent of the surface area of the web is embossed. Nonetheless, significantly greater amounts of the surface area of the web can be embossed.

The webs can be embossed over a wide range of temperatures. The webs are generally embossed at temperatures within the range of from about 20° C. to about 150° C. The webs are suitably embossed by passing through a nip defined by embossing rolls. For example, webs having a bulk thickness of from about 0.05 inch to about 0.2 inch can be embossed by passing through a nip of about 0.01 inch to about 0.04 inch applying a pressure of from about 400 to about 4000 pounds-force. The webs may be embossed either with or without the wrap sheet present. Calendering or embossing the webs is believed to assist in formation of bonds between the fibrous material and/or the absorbent material.

It is desired that the absorbent webs of the present invention generally contain the absorbent material. Specifically, it is desired that the webs have a shakeout value of less than about 250 milligrams, desirably of less than about 150 milligrams, preferably of less than about 25 milligrams, and most preferably of less than about 10 milligrams, as determined as set forth below in connection with the examples.

It is also desired that the absorbent webs are generally flexible. Specifically, it is desired that the webs have a Gurley stiffness value of less than about 1500 milligrams, desirably of less than about 1000 milligrams, preferably of less than about 800 milligrams, and most preferably of less than about 600 milligrams, as determined as set forth below in connection with the examples.

Applicants have found that absorbent webs having shakeout values of less than about 25 milligrams and Gurley stiffness values of less than about 600 milligrams are particularly desirable for use in absorbent products.

The webs according to the present invention can be made in a wide variety of basis weights. The webs suitably have a basis weight of from about 50 to about 2000, preferably of from about 100 to about 700, and most preferably of from about 250 to about 500 grams per square meter. Similarly, the webs may be have any desired thickness. The webs suitably have a thickness, determined under a load of about 0.2 psi, of from about 0.02 inch to about 0.5 inch, preferably of from about 0.02 inch to about 0.2 inch, and most preferably of from about 0.04 inch to about 0.15 inch.

When the mixture of fibrous material, absorbent material and water comprises more than about 50 weight percent absorbent material, thin absorbent webs can be made. Correspondingly, thin absorbent products can be made from the absorbent webs. When the mixture comprises more than about 50 weight percent of absorbent material, movement of liquid through the web depends, to a large extent, on capillaries created between the particles of absorbent material. At lower concentrations of absorbent material, movement of the liquid can occur through capillaries created by the fibrous material and/or absorbent materials. Movement of a liquid through the web is generally desirable in order to maximize utilization of the absorbent material.

When the mixture comprises more than about 50 weight percent of absorbent material, it is desirable to use an absorbent material which is capable of maintaining a capillary structure which allows for the movement of fluid. Accordingly it is desirable to use an absorbent material which is capable of resisting deformation when placed under a load, such as the weight of an infant. If deformation occurs under a load, the capillary structure is destroyed. If deformation is resisted, the capillary structure remains open. Specifically, it is desirable to employ an absorbent material having a deformation under load of less than about 1.5 millimeters, desirably of less than about 0.6 millimeter, and preferably of less than about 0.4 millimeter. The method by which deformation under load is determined is set forth below in connection with the examples.

Further, when the mixture comprises more than about 50 weight percent of absorbent material, it is desired that the absorbent material have the ability to absorb while under a load. The ability of an absorbent material to absorb under a load is quantified as the Absorbency Under Load. The method by which Absorbency Under Load is determined is set forth below in connection with the examples. As a general rule, it is desirable to use an absorbent material with an Absorbency Under Load of at least about 15 grams per gram, beneficially of at least about 20 grams per gram, and preferably of at least about 27 grams per gram.

Figure 2:
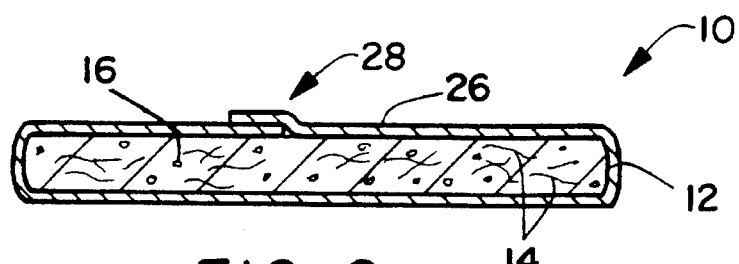
FIG. 2 illustrates an absorbent composite according to a second embodiment of the present invention.
Figure 3:
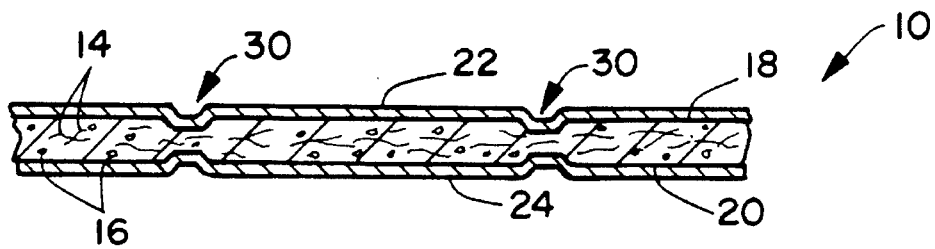
FIG. 3 illustrates the absorbent composite of FIG. 1 after embossing.

Referring now to the figures, FIG. 1 illustrates one embodiment according to the present invention. FIG. 1 illustrates an absorbent composite 10 comprising a web 12 formed from fibrous material 14 and absorbent material particles 16. The web 12 defines planar surfaces 18 and 20 having applied thereto tissue sheets 22 and 24. Referring now to FIG. 2, an absorbent composite according to a second embodiment of the present invention is illustrated. An absorbent composite 10 is shown comprising web 12 formed from fibrous materials 14 and absorbent material particles 16. The web 12 is completely surrounded by wrap sheet 26 which overlaps in area 28. FIG. 3 illustrates the absorbent composite illustrated in FIG. 1 which has been embossed at points 30.

In a second aspect, the present invention concerns a method for making an absorbent composite. The method comprises the steps of forming an absorbent web. The web comprises a mixture of from about 0 to about 45 weight percent, based on total mixture weight, of a fibrous material; from about 40 to about 85 weight percent, based on total mixture weight, of a particulate, water-swellable, generally water-insoluble absorbent material capable of absorbing at least about 10 times its own weight in water; and from about 15 to about 30 weight percent of water. At least a portion of a surface of said absorbent web is surrounded with a liquid-permeable wrap sheet. The absorbent web is then compressed such that bonding occurs between the fibrous material and absorbent material. The steps of the method are preferably sequential but may be nonsequential.

Figure 4:
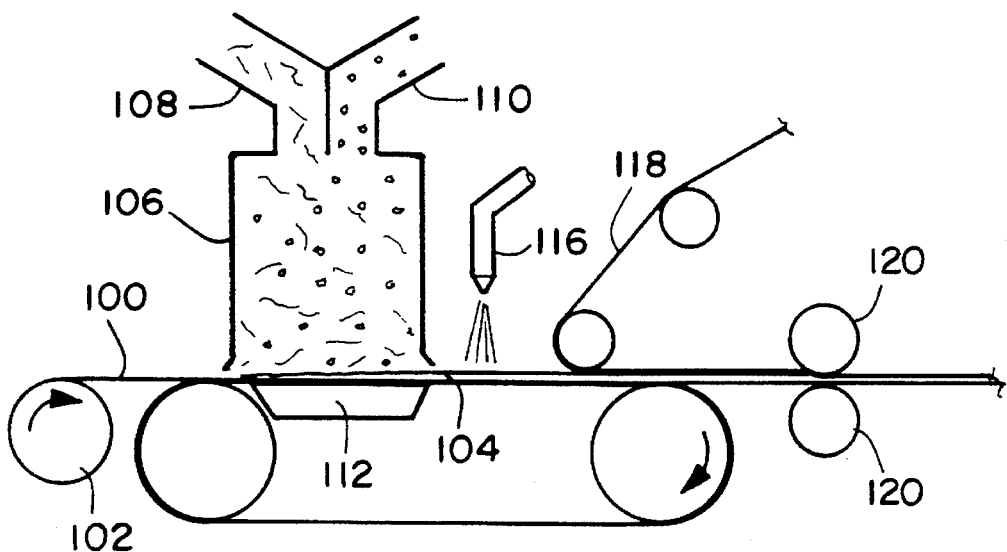
FIG. 4 is a schematic representation of a method for producing an absorbent composite according to the present invention.

The method of the present invention can best be understood by reference to FIG. 4 which is a schematic illustration of a process according to the present invention. With reference to FIG. 4, a wrap sheet 100 is provided from supply roll 102. The wrap sheet 100 is placed on a porous forming surface 104 and passes under a deposition chamber 106. Deposition chamber 106 includes supply means 108 through which a fibrous material is supplied and supply means 110 through which a particulate absorbent material is supplied. The fibrous material and particulate absorbent material are mixed in deposition chamber 106 and are deposited on the wrap sheet due to the presence of a vacuum being drawn by vacuum means 112. As web 114 passes from under deposition chamber 106, water is applied to web 114 by spray nozzle 116. A second wrap sheet 118 is then applied to the upper surface of web 114 and the absorbent composite passed between patterned embossing rolls 120.

Those skilled in the art will recognize that the water may be applied at numerous points during the manufacturing process. The water may be applied in the form of a liquid or gas. It is preferred that the water be applied in the form of a liquid due to ease of addition, handling and cost.

The composites of the present invention are suitably employed in absorbent products such as diapers, training pants, feminine care products, adult incontinent garments, and the like. When the composites are employed in diapers, the composites are suitably sandwiched between a liquid-pervious bodyside liner and an outer cover.

Test Methods

Absorbency Under Load

The Absorbency Under Load (AUL) is a test which measures the ability of an absorbent material to absorb a liquid (0.9 weight percent solution of sodium chloride in distilled water) while under an applied load or restraining force.

Figure 5:
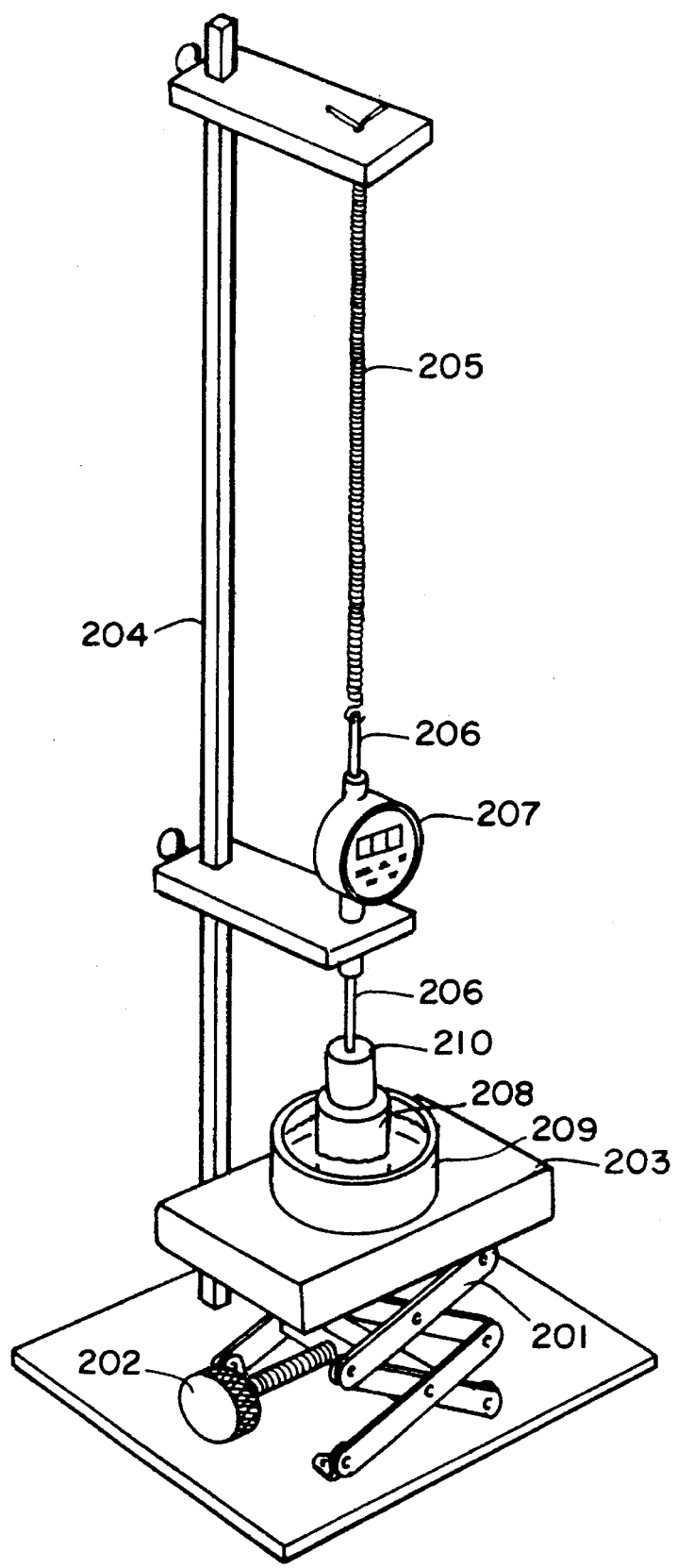
FIGS. 5–9 illustrate equipment used in determining certain physical properties of the absorbent material of the absorbent composites of the present invention.

Referring to FIG. 5, the apparatus and method for determining AUL will be described. Shown is a perspective view of the apparatus in position during a test. Shown is a laboratory jack 201 having an adjustable knob 202 for raising and lowering the platform 203. A laboratory stand 204 supports a spring 205 connected to a modified thickness meter probe 206, which passes through the housing 207 of the meter, which is rigidly supported by the laboratory stand. A plastic sample cup 208, which contains the absorbent material sample to be tested, has a liquid-permeable bottom and rests within a Petri dish 209, which contains the saline solution to be absorbed. A weight 210 rests on top of a spacer disc (not visible) resting on top of the absorbent material sample (not visible).

The sample cup consists of a plastic cylinder having a 1 inch inside diameter and an outside diameter of 1.25 inch. The bottom of the sample cup is formed by adhering a 100 mesh metal screen, having 150 micron openings, to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe located on the top of the meter housing is also removed to enable attachment of the probe to the suspension spring 205 (available from McMaster-Carr Supply Co., Chicago, Ill., Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the absorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 gram weight is then placed on top of the spacer disc, thereby applying a load of 0.3 pounds per square inch. The sample cup is placed in the Petri dish and the platform of the laboratory jack raised up until it contacts the tip of the probe. The meter is zeroed. A sufficient amount of saline solution is added to the Petri dish (50–100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 60 minutes is the AUL value, expressed as grams saline solution absorbed per gram of absorbent. If desired, the readings of the modified thickness meter can be continuously input to a computer (Mitutoyo Digimatic Miniprocessor DP-2 DX) to make the calculations and provide AUL readings. As a cross-check, the AUL can also be determined by determining the weight difference between the sample cup before and after the test; the weight difference being the amount of solution absorbed by the sample.

Shake Out Test

A test sample about 3.5 inches×13 inches is provided and weighed. The sample to be tested is mounted on a lint-free blotter stock or card stock having dimensions of 6 inches×15 inches. The sample to be tested is mounted to the blotter stock by placing the sample to be tested in the center of an 8 inch×17 inch piece of 0.4 ounce per square yard spunbond material, such as that typically used as bodyside liners for disposable diapers. The blotter stock is placed on top of and covers the sample to be tested, and the spunbond material wrapped around and adhered to the surface of the blotter stock opposite the sample to be tested. The spunbond material is porous, such that the individual fibers and particles of absorbent material, from which the sample to be tested is formed, can pass through the spunbond material. The sample to be tested is then placed in an RX-24 shaker, commercially available from Tyler Co., and shaken for a period of five minutes. The shaker is modified to hold a basket in which the test sample can be located. Debris falling from the sample to be tested is collected into filter cassettes and weighed. The collected debris is subjected to chemical analysis to determine the amount of absorbent material collected. The amount of absorbent material collected, in milligrams, is reported as the shakeout value.

Deformation Under Load

In order to determine the Deformation Under Load for the absorbent materials of this invention, a synthetic urine was used as the absorbed fluid to closely approximate in-use performance in diapers. The synthetic urine composition referenced herein comprises 1.0 gram methyl paraben, 0.68 grams monobasic potassium phosphate ($KH_2PO_4$), 0.31 grams monobasic calcium phosphate monohydrate ($CaH_4(PO_4)_2H_2O$), 0.48 gram magnesium sulphate heptahydrate ($MgSO_4$ $7H_2O$), 1.33 grams potassium sulphate ($K_2SO_4$), 1.24 grams tribasic sodium phosphate dodecahydrate ($Na_3PO_4$ $12H_2O$) 4.44 grams sodium chloride (NaCl), 3.16 grams potassium chloride (KCl), 8.56 grams of urea ($CO(NH_2)_2$), 1.0 gram Germall 115 preservative (commercially available from Santell Chemical Company, Chicago, Ill.), and 0.1 gram Pluronic 10R8 surfactant (a nonionic surfactant commercially available from BASF-Wyandotte Corporation). The components are added to 900 milliliters of distilled water in the order given and each dissolved before the next component is added. The solution is finally diluted to 1 liter and has a surface tension in the range of 54–58 dynes per centimeter.

The Deformation Under Load is essentially a measure of a gelled absorbent material's ability to resist compression deformation under a controlled load. Briefly, the test involves the incomplete saturation of an absorbent material with a fixed amount of synthetic urine (25 grams of urine per gram of absorbent material), compressing the absorbent material under a light load, and then measuring the deformation of the sample under a heavier load, all under ambient conditions. Referring to FIGS. 6–9, the test apparatus and procedure will be described in detail.

Figure 6:
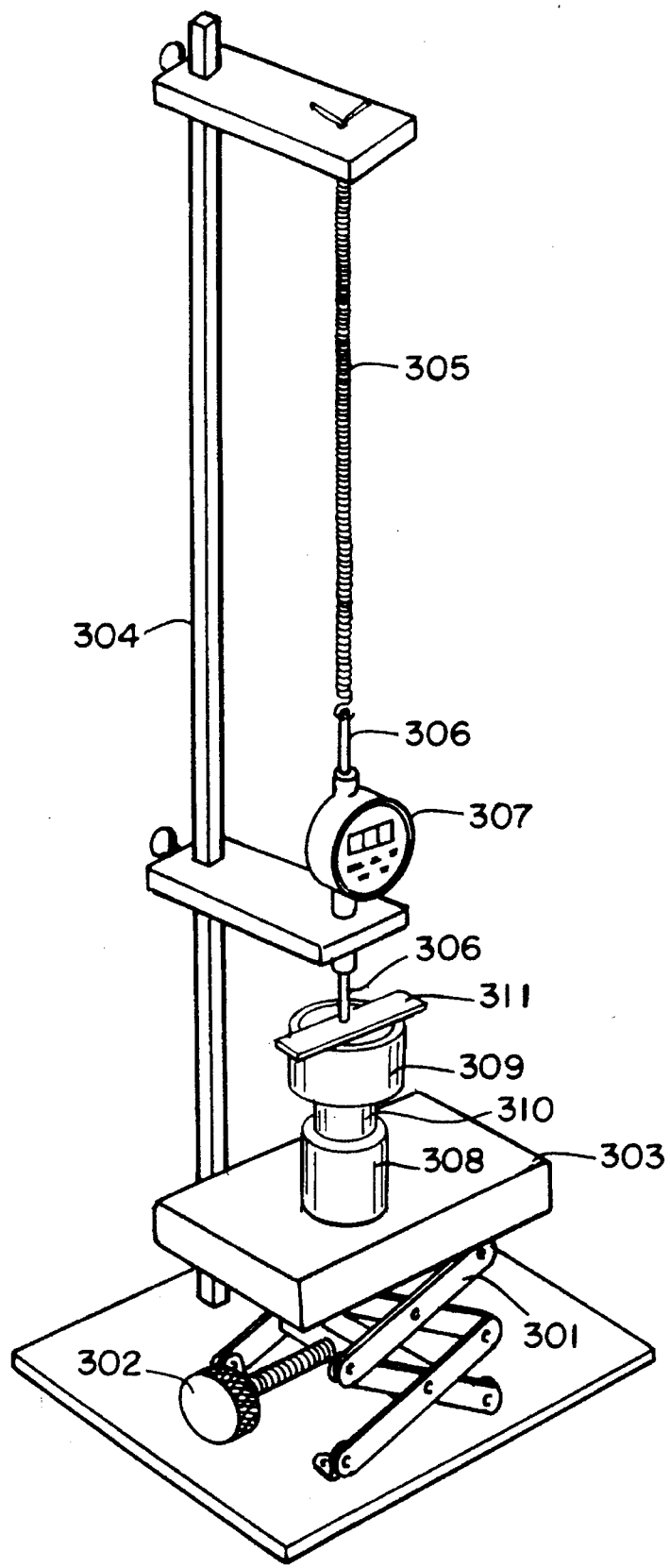

FIG. 6 is a perspective view of the test apparatus during testing. Shown is a laboratory jack 301 having an adjustable knob 302 for raising and lowering the platform 303. A laboratory stand 304 supports a suspension spring 305 connected to the probe 306 of a modified thickness meter (described below). The housing 307 of the thickness meter is rigidly affixed to and supported by the laboratory stand. The probe extends through the housing of the thickness meter, which detects any movement of the probe. Also shown is a plastic sample cup 308, a plastic weight cup 309 having a cylindrical foot 310, and a glass slide 311.

The modified thickness meter, which is used to measure the deformation of the sample under load, is a Mitutoyo Digimatic Indicator, IDC Series 543, Model 543-180, having a range of 0–0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free-falling probe which has a downward force of about 27 grams. In addition, the cap over the top of the probe, located on the top of the meter housing, is also removed to enable attachment of the probe to the suspension spring 305 (Available from McMaster-Carr Supply Co., Chicago, Ill., Item No. 9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

Figure 7:
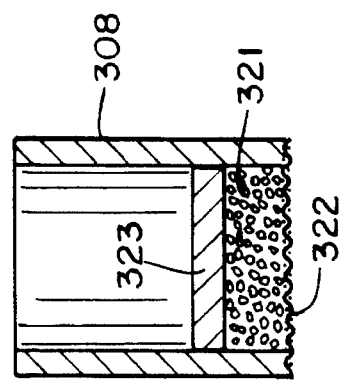

FIG. 7 is a sectional view of the sample cup 308 into which the absorbent particles 321 to be tested are placed.

The sample cup is a plastic cylinder having a 1 inch inside diameter and an outside diameter of 1.25 inch. The bottom of the cup is formed by adhering (gluing) a 100 mesh metal screen 322, having 150 micron openings, to the end of the cylinder. A 0.1600 gram (±0.0005 gram) sample of the absorbent material, which has been sieved to a particle size between 300 and 600 microns, is placed into the sample cup and evenly spread over the screen bottom. (Fibrous absorbent materials need not be sieved.) The sample is then covered with a plastic spacer disc 323 (having a diameter of 0.990–0.995 inch) to protect the sample from being disturbed during the test.

Figure 8:
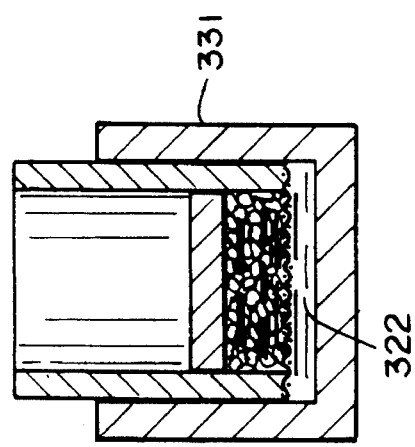

The sample cup is then slowly lowered into a plastic reservoir cup 331 containing 4.00 grams of synthetic urine 332, as illustrated in the sectional view of FIG. 8, being careful not to disrupt the absorbent material with escaping air. The inside diameter of the reservoir cup is only slightly greater than 1.25 inch, in order to provide a snug fit between the sample cup and the reservoir cup, sufficient to prevent the synthetic urine from escaping between the sample cup and the reservoir cup. The sample cup is lowered to the bottom of the reservoir cup such that the synthetic urine is gently forced up through the screen to evenly contact the absorbent material. The sample cup remains inside the reservoir cup for 30 minutes to ensure that all of the synthetic urine is absorbed by the sample.

Figure 9:
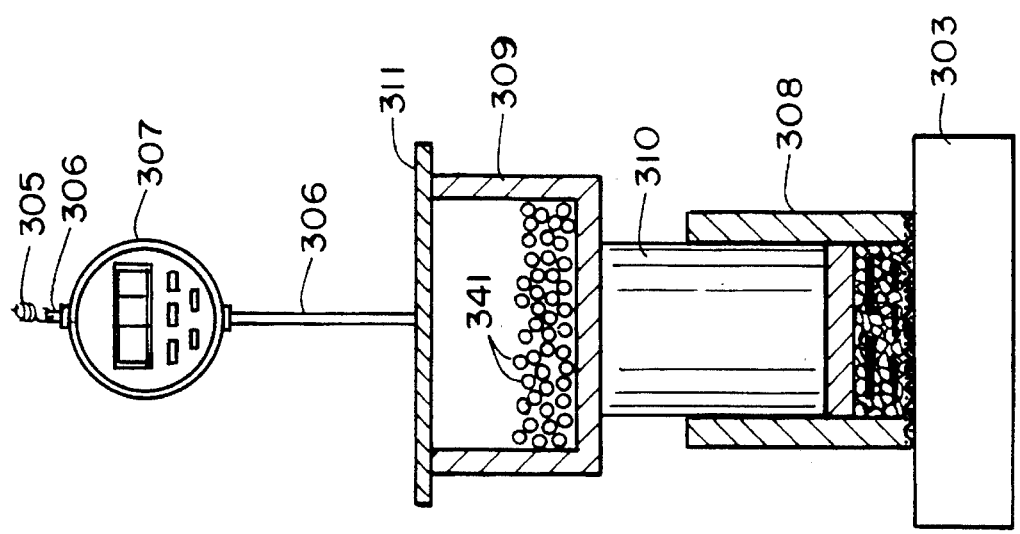

The sample cup is removed from the reservoir cup and placed on the platform 303 of the laboratory jack, as illustrated in the sectional view of FIG. 9. The plastic weight cup 309 having a cylindrical foot 310 is used to apply a known load to the sample. The cylindrical foot has an outside diameter of 0.990–0.995 inch. The bottom of the foot is solid. The weight cup is also provided with a glass slide 311 which bridges the open top of the weight cup and provides a flat surface against which the probe 306 of the thickness meter is positioned. The combined total weight of the weight cup, including the foot, the glass slide and the spacer disc in the sample cup, is 100 grams. If the total weight falls short of 100 grams, some lead shot can be placed inside the weight cup to bring the combined weight up to the 100 gram level.

When testing the sample, the foot of the weight cup is placed inside the sample cup, and the platform is raised up until the probe of the thickness meter contacts the glass slide and then is raised up slightly further to give the probe enough play to return toward its initial position during the subsequent test. For most materials, the probe should be raised about 3 millimeters above its normal resting point. The load on the sample at this point is 0.3 pounds per square inch. The thickness meter is then set to zero, and 200 grams of lead shot 341 or other suitable weight are added to the weight cup, bringing the load up to 300 grams or 0.9 pounds per square inch. The downward distance of travel of the probe from the zero point, which is read after the rate of change is less than 0.006 millimeters in two minutes, expressed in millimeters, is the Deformation Under Load of the sample. Normally the reading can be taken within 10 to 20 minutes.

Saturated Retention Capacity

The saturated retention capacity is a measure of the total absorbent capacity of absorbent composites of the present invention. The saturated retention capacity is determined as follows. The composite to be tested is weighed and submerged in an excess quantity of room temperature ~23° C.) synthetic urine described above in connection with the Deformation Under load test. The composite is allowed to remain submerged for 5 minutes. After 5 minutes, the composite is removed from the urine and placed on a Teflon™ coated fiberglass screen having 0.25 inch openings (commercially available from Taconic Plastics Inc. Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The composite is weighed. The amount of fluid retained by the composite being tested is determined by subtracting the dry weight of the composite from the wet weight of the composite (after application of the vacuum). For relative comparisons, this value is divided by the weight of the composite to give the saturated retention capacity in grams of fluid retained per gram of tested composite.

Gurley Stiffness Test

The stiffness of the absorbent composites, according to the present invention, is determined using a Gurley Digital Stiffness Tester commercially available from Teledyne Gurley, Troy, N.Y. The Gurley Stiffness Tester measures the force required to bend a specific test sample under specific conditions. The test samples employed have a dimension of 1 inch by 3½ inches. The test samples are centered over the pendulum such that exactly 0.25 inch overlaps the top of the pendulum and exactly 0.25 inch is held in the jaws. The test sample is brought into contact with the pendulum. Both a left scale reading and a right scale reading are obtained and averaged. The reported value is the average of the left and right scale readings. It is understood that, for different basis weight materials, the exact weight applied and its location on the pendulum may be varied as necessary to obtain meaningful values.

EXAMPLES

A number of absorbent composites are formed from fibrous wood pulp fluff and particulate, water-swellable, generally water-insoluble absorbent material. The wood pulp fluff employed is a mixture of 20 percent hard wood pulp and 80 percent soft wood pulp. One of two types of absorbent material are employed. Absorbent material A is a partially neutralized sodium salt of polyacrylic acid formed through a gel (solution) polymerization process. The absorbent material has an Absorbency Under Load value of 29.9 grams per gram and a Deformation Under Load of 0.382 millimeter. The absorbent material is in the form of particulates screened to have a particle size within the range of from about 170 to about 850 microns. The absorbent material is commercially available from Hoechst-Celanese Corporation under the trade designation IM5000P. Absorbent material B is a partially neutralized sodium salt of polyacrylic acid formed through a suspension polymerization process. The absorbent material has an Absorbency Under Load value of 24.5 grams per gram and a Deformation Under Load of 0.241 millimeter. Accordingly, the particles of absorbent material are generally spherical. The particles have an average diameter of from about 170 to about 850 microns. The absorbent material is commercially available from Norsolor Corporation under the trade designation NORSACRYL™ B41S.

Various relative amounts of fluff and absorbent material are air laid to form absorbent composites. The combination of wood pulp fluff and absorbent material is air laid on a single ply, creped tissue having a basis weight of 17 grams per square meter and being formed from cellulosic fibers. After air laying the wood pulp fluff and absorbent material on the tissue, water is added to the composites by spraying, such that an essentially uniform application of water is applied to the wood pulp fluff and absorbent material. The water is sprayed through a UNIJET™ flat spray nozzle having an orifice of 0.018 inch commercially available from Spraying Systems Company under the trade designation UNIJET™ Flat Spray Nozzle Type 500050. The nozzle is located approximately 12 inches above the surface of the absorbent composite. After application of the water, a second tissue is laid on top of the composites and the first tissue is C-folded, such that the wood pulp fluff and absorbent material are completely surrounded by tissue.

After application of the water and C-folding, the absorbent composites are embossed by passing through a pair of embossing rolls. One of the embossing rolls is flat and is heated to a temperature of 60° C. The other embossing roll is patterned, such that about 4 percent of the surface of the absorbent composite is embossed. The gap between the embossing rolls is varied. The embossing pattern forms ½ inch squares. The embossing areas have a depth of 0.25 inch.

A number of absorbent composites are formed having varying concentrations of wood pulp fluff, absorbent material, and water. Additionally, the type of absorbent material and bonding gap are varied. After formation, the absorbent composites are subjected to physical property testing. The exact components employed in forming the absorbent composites and their physical properties are set forth in Table 1.

What is claimed is:

1. An absorbent composite, said absorbent composite comprising:

an absorbent web comprising an airlaid mixture of between 0 and about 45 weight percent, based on total mixture weight, of a fibrous material; from about 40 to about 85 weight percent, based on total mixture weight, of a particulate, water-swellable, generally water-insoluble absorbent material capable of absorbing at least about 10 times its own weight in water; and from about 15 to about 30 weight percent, based on total mixture weight, of water; wherein the fibrous material and absorbent material are bonded such that the absorbent material is substantially contained within said absorbent web.

2. The absorbent composite according to claim 1 wherein said absorbent material is selected from a group consisting of alkali metal salts of polyacrylic acid, polyacrylamides, polyvinyl alcohol, ethylene maleic anhydride copolymers, polyvinyl ethers, polyvinylmorpholinone, polymers and copolymers of vinyl sulfonic acid, polyacrylates, polyacrylamides, polyvinylpyrridine, hydrolyzed acrylonitrile grafted starch, acrylic acid grafted starch, isobutylene maleic anhydride copolymers and mixtures thereof.

3. The absorbent composite according to claim 1 wherein said mixture comprises between 0 and about 35 weight

TABLE 1

| Sample No. | Wt. % Fluff | Wt. % Absorbent | Wt. % Water | Type of Absorbent | Bonding Gap (inch) | Shakeout Value (mg) | Saturated Capacity (g/g) | Gurley Stiffness (mgs) | Basis Wt. (gsm) | Thickness (inches) |
|---|---|---|---|---|---|---|---|---|---|---|
| 1* | 18.9 | 75.5 | 5.6 | A | 0.017 | 675.0 | 22.8 | 54.9 | 406 | 0.106 |
| 2 | 17 | 68.2 | 14.8 | A | 0.017 | 5.8 | 23.1 | 493 | 387 | 0.067 |
| 3 | 16.2 | 64.9 | 18.9 | A | 0.017 | 2.3 | 22.3 | 590 | 391 | 0.064 |
| 4* | 37.8 | 56.7 | 5.5 | A | 0.017 | 259.0 | 21.8 | 111 | 390 | 0.11 |
| 5 | 34.3 | 51.5 | 14.2 | A | 0.017 | 2.5 | 21.5 | 768 | 414 | 0.076 |
| 6 | 32.6 | 49.0 | 18.4 | A | 0.017 | 1.7 | 20.3 | 722 | 408 | 0.08 |
| 7* | 56.6 | 37.8 | 5.6 | A | 0.017 | 82 | 17.6 | 266 | 375 | 0.152 |
| 8* | 52.3 | 34.9 | 12.8 | A | 0.017 | 0.57 | 16.9 | 438 | 418 | 0.11 |
| 9* | 50.6 | 33.7 | 15.7 | A | 0.017 | 0.92 | 16.4 | 496 | 440 | 0.106 |
| 10* | 76.2 | 19.0 | 4.8 | A | 0.017 | 74.7 | 15.2 | 256 | 451 | 0.189 |
| 11* | 70.4 | 17.6 | 12.0 | A | 0.017 | 0.52 | 13.6 | 508 | 442 | 0.135 |
| 12* | 67.2 | 16.8 | 16.0 | A | 0.017 | 0.62 | 14.3 | 501 | 470 | 0.134 |
| 13 | 16.9 | 67.8 | 15.3 | A | 0.022 | 5.8 | 22.3 | 354 | 401 | 0.064 |
| 14 | 16.9 | 67.6 | 15.5 | A | 0.012 | 5.3 | 21.6 | 476 | 385 | 0.073 |
| 15 | 16.2 | 64.6 | 19.2 | B | 0.017 | 1297.0 | 20.0 | 33 | 441 | 0.083 |
| 16 | 33.2 | 49.8 | 17.0 | B | 0.017 | 196.0 | 19.1 | 96 | 403 | 0.09 |
| 17* | 51.1 | 34.1 | 14.8 | B | 0.017 | 189.0 | 15.1 | 187 | 418 | 0.127 |
| 18* | 68.6 | 17.2 | 14.2 | B | 0.017 | 8.0 | 14.1 | 273 | 460 | 0.143 |
| 19 | 16.9 | 67.6 | 15.5 | A | 0.007 | 1.7 | 22.9 | 542 | 404 | 0.062 |

*Not an example of the present invention

As can be seen from reference to Table 1, the addition of from about 15 to about 30 weight percent water greatly improves the ability of an absorbent composite to contain a particulate superabsorbent material. This is clearly seen by reference to Sample Nos. 1–3 and 4–6. With reference to Sample Nos. 15–18, it is seen that the spherical superabsorbent particles (Type B) are not as well contained as the non-spherical, irregularly-shaped particles of superabsorbent Type A. Nonetheless, improved containment is achieved through the addition of 15–30 weight percent of water.

Having described specific embodiments of the invention, it will be readily apparent that various changes and modifications may be made without departing from the spirit of the invention. All such changes and modifications are contemplated as being within the scope of the present invention as defined by the following claims.

percent of said fibrous material and from about 50 to about 85 weight percent of said particulate absorbent material.

4. The absorbent composite according to claim 1 wherein said mixture comprises from about 5 to about 30 weight percent of said fibrous material and from about 55 to about 80 weight percent of said particulate absorbent material.

5. The absorbent composite according to claim 1 wherein said mixture comprises from about 10 to about 25 weight percent of said fibrous material and from about 60 to about 80 weight percent of said particulate absorbent material.

6. The absorbent composite according to claim 1 wherein said absorbent web has a shakeout value of less than about 250 milligrams.

7. The absorbent composite according to claim 1 wherein said absorbent web has a shakeout value of less than about 150 milligrams.

8. The absorbent composite according to claim 1 wherein said absorbent web has a shakeout value of less than about 25 milligrams.

9. The absorbent composite according to claim 1 wherein said absorbent web is at least partially surrounded by a wrap sheet.

10. The absorbent composite according to claim 9 wherein said absorbent web is completely surrounded by said wrap sheet.

11. The absorbent composite according to claim 1 wherein said absorbent web is embossed.

12. The absorbent composite according to claim 11 wherein said absorbent web is embossed at a temperature of from about 20° C. to about 150° C. over an area of less than about 10 percent of the surface area of said absorbent web.

13. The absorbent composite according to claim 12 wherein said absorbent web is embossed over an area less than about 8 percent of the surface area of said absorbent web.

14. The absorbent composite according to claim 1 wherein said absorbent web has a Gurley stiffness of less than about 1500 milligrams.

15. The absorbent composite according to claim 1 wherein said mixture comprises water in an amount of from about 15 to about 25 weight percent.

16. The absorbent composite according to claim 1 wherein said mixture comprises water in an amount of from about 15 to about 22 weight percent.

17. The absorbent composite according to claim 1 wherein said fibrous material is a cellulosic fiber.

18. An absorbent composite, said composite comprising:

an absorbent web formed from an airlaid mixture comprising between 0 and about 45 weight percent, based on total mixture weight, of a cellulosic fibrous material; from about 40 to about 85 weight percent, based on total mixture weight, of a particulate, water-swellable, generally water-insoluble absorbent material capable of absorbing at least about 10 times its own weight in water and having a deformation under load of less than about 1.5 millimeters; and water in an amount of from about 15 to about 30 weight percent, based on total mixture weight, said water being added to said absorbent composite in the form of a liquid wherein the fibrous material and absorbent material are bonded such that said absorbent web has a shakeout value of less than about 250 milligrams and a Gurley stiffness of less than about 1500 milligrams.

19. The absorbent composite according to claim 18 wherein said web is at least partially surrounded by a liquid-permeable wrap sheet.

20. The absorbent composite according to claim 18 wherein said absorbent material has an absorbency under load of at least about 15 grams per gram.

* * * * *